United States Patent
Pfohmann et al.

(10) Patent No.: US 10,576,035 B2
(45) Date of Patent: Mar. 3, 2020

(54) COMPOSITION, PROCESS, AND DEVICE FOR TEMPORARY COLORING OF KERATIN FIBERS

(71) Applicant: Kao Corporation, Tokyo (JP)

(72) Inventors: Stefanie Pfohmann, Darmstadt (DE); Melina Sulzbach, Darmstadt (DE); Christine Cajan, Darmstadt (DE); Sabine Schmid, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/118,817

(22) Filed: Aug. 31, 2018

(65) Prior Publication Data

US 2019/0192415 A1    Jun. 27, 2019

(30) Foreign Application Priority Data

Dec. 21, 2017  (EP) ................................. 17209493
Aug. 29, 2018  (EP) ................................. 18191439

(51) Int. Cl.
| | |
|---|---|
| *A61Q 5/10* | (2006.01) |
| *A61K 8/91* | (2006.01) |
| *A61Q 5/06* | (2006.01) |
| *A61K 8/89* | (2006.01) |
| *A61K 8/04* | (2006.01) |
| *A61K 8/19* | (2006.01) |
| *A61K 8/20* | (2006.01) |
| *A61K 8/25* | (2006.01) |
| *A61Q 5/00* | (2006.01) |

(52) U.S. Cl.
CPC .............. *A61K 8/91* (2013.01); *A61K 8/046* (2013.01); *A61K 8/19* (2013.01); *A61K 8/20* (2013.01); *A61K 8/25* (2013.01); *A61K 8/89* (2013.01); *A61Q 5/00* (2013.01); *A61Q 5/06* (2013.01); *A61Q 5/065* (2013.01); *A61K 2800/31* (2013.01); *A61K 2800/42* (2013.01); *A61K 2800/43* (2013.01); *A61K 2800/432* (2013.01)

(58) Field of Classification Search
CPC . A61Q 5/00; A61K 8/19; A61K 8/585; A61K 8/046; A61K 8/25; A61K 2800/31; A61K 8/89; A61K 2800/42; A61K 9/12; A61K 2800/432
See application file for complete search history.

(56) References Cited

U.S. PATENT DOCUMENTS

| | | |
|---|---|---|
| 5,849,316 A | 12/1998 | Mellul et al. |
| 2009/0041683 A1 | 2/2009 | Molenda et al. |
| 2009/0226381 A1 | 9/2009 | Maillefer et al. |
| 2010/0047202 A1* | 2/2010 | Goddinger ............. A61K 8/731 424/70.12 |
| 2011/0174329 A1 | 7/2011 | Seng et al. |
| 2012/0315232 A1* | 12/2012 | Vic ......................... A61K 8/02 424/61 |
| 2017/0216193 A1 | 8/2017 | Goutsis et al. |

FOREIGN PATENT DOCUMENTS

| | | |
|---|---|---|
| DE | 10 2014 221 536 A1 | 4/2016 |
| EP | 0 704 205 A1 | 4/1996 |
| EP | 1 997 472 A1 | 12/2008 |
| EP | 2 022 479 A1 | 2/2009 |
| EP | 2 090 295 A1 | 8/2009 |
| FR | 2 932 378 A1 | 12/2009 |
| JP | 2010-163390 A | 7/2010 |
| JP | 2017-114815 A | 6/2017 |
| WO | WO 2017/099158 A1 | 6/2017 |

OTHER PUBLICATIONS

Stic Search Report dated Jul. 18, 2019.*
Extended European Search Report dated Jun. 26, 2018 in Patent Application No. 17209493.0.
"Take 2 Dry Shampoo", Farouk Systems, http://www.gnpd.com, XP002782044, Dec. 2015, 2 pages.
"Dry Shampoo", Farouk Systems, http://www.gnpd.com, XP002782045, Nov. 2015, 2 pages.

* cited by examiner

*Primary Examiner* — Eisa B Elhilo

(74) *Attorney, Agent, or Firm* — Oblon, McClelland, Maier & Neustadt, L.L.P.

(57) ABSTRACT

The present invention is directed to an aerosol cosmetic composition, temporary keratin fiber dyeing method, and device which employ pigments and organopolysiloxane graft polymers in an environment with low water content. Good dyeing properties combined with wear and water resistance as well as good removability upon 1 shampooing were found.

18 Claims, No Drawings

COMPOSITION, PROCESS, AND DEVICE FOR TEMPORARY COLORING OF KERATIN FIBERS

FIELD OF THE INVENTION

The present invention is directed to an aerosol composition which confers temporary color to keratin fibers and allows for optional temporary styling upon coloring. Furthermore, a process for dyeing and optional styling, and a device is disclosed.

BACKGROUND OF THE INVENTION

Fashionable customers desire to change their appearance according to quickly changing fashion trends. A quite impressive way to achieve a noticeable result is to change the hair color, especially from dark to brighter tones. However, common permanent coloring services have the disadvantage that the hair color lasts longer than the fashion trend. Consequently the market offers temporary hair colors which allow for a changing color depending on the day-to-day mood. An easy way to apply temporary hair colors is spraying them from an aerosol can.

A common ingredient in temporary hair colors is titanium dioxide (Mintel #4669407) which often delivers a satisfactory brightening of the keratin fibers, but has a poor reputation for potentially causing cancer when inhaled (press release ECHA/PR/17/10). Thus, the use of titanium dioxide in aerosol products is to be further reduced.

Another common problem with temporary colors applied as an aerosol is their low resistance against water and mechanical wear. Consequently many customers are dissatisfied with undesired staining of their cloths and pillows and blurring of the color on rainy days.

EP1997472 discloses compositions and a process for coloring keratin fibers comprising pigments in an aqueous environment and tackles the problem of wear resistance. EP0704205 and FR2932378 disclose anhydrous compositions comprising pigments on the basis of linear/cyclic silicones and tackle the problem of wear resistance as well.

In JP2010163390 an anhydrous aerosol composition comprising carbon black as pigment and organopolysiloxane graft polymer is disclosed. However, the weight ratio of liquid to propellant is distinctly different.

Another possibility of application is disclosed in JP2017114815 which is immersing a hair streak with the cosmetic coloring composition. However, this approach delivers very wet keratin fibers which need an extended period of time for drying.

In summary, none of the aforementioned prior art documents solve the addressed problems in a satisfactory manner. Moreover, the prior art is silent on the core of the present invention.

SUMMARY OF THE INVENTION

Inventors of the present invention have unexpectedly found out that an aerosol composition comprising one or more organopolysiloxane graft polymer(s), one or more pigment(s), specific organic solvents, and propellant exceeding a certain weight threshold deliver a quickly drying temporary hair color composition which exhibits a high brightening effect, superior pigment deposition onto keratin fibers, good film forming properties onto keratin fibers, good wear and water resistance, and a good and natural cosmetic feel of the treated keratin fibers. However, as high water resistance is a highly important feature of the present invention, it simultaneously allows for removal of the temporary hair color by shampooing of the keratin fibers with commercially available shampoos. This effect is highly desired by customers who wish to change their hair color on a daily basis. Additionally, during spraying of the aerosol it is achieved by the invention to yield small droplet sizes to ensure a more uniform distribution onto keratin fibers. Moreover, as alternative for titanium dioxide with its excellent brightening properties, another brightening pigment, namely bismuth oxychloride, was found to deliver good results on keratin fibers.

DETAILED DESCRIPTION OF THE INVENTION

Therefore, the first object of the present invention is a cosmetic aerosol composition for keratin fibers, preferably human keratin fibers, more preferably for human hair, characterized in that it comprises:
  One or more organopolysiloxane graft polymers,
  One or more pigment,
  One or more cosmetically acceptable organic solvent with a boiling point in the range of more than 50° C. to 120° C. under atmospheric conditions,
  One or more propellant(s) at a total concentration of at least 50% by weight, calculated to the total of the composition,
wherein the composition comprises less than 5% by weight of water, calculated to the total of the composition, preferably it is anhydrous.

The second object of the present invention is a method for dyeing keratin fibers, preferably human keratin fibers, more preferably human hair, characterized in that it comprises the following steps:
a) optionally washing and drying the keratin fibers,
b) applying a composition as defined above to dry keratin fibers,
c) optionally treating the keratin fibers with a comb, brush, flat-iron and/or round-iron at a temperature in the range of 50° C. to 230° C.

The third object of the present invention is an aerosol device comprising the composition as defined above.

The further object of the present invention is a kit-of-parts comprising the composition as defined above.

The term organopolysiloxane graft polymer within the meaning of the present invention denotes a polymer which has an organopolysiloxane segment as the main chain and/or side chain. Preferably the organosiloxane segment is within the main chain and the graft side chains comprise non-silicone moieties.

It is preferred that the keratin fibers after step b) of the second embodiment of the present invention are dried at room temperature without employing a heating appliance.

The term anhydrous within the meaning of the present invention denotes a composition which is free of added water. The term does not exclude bound crystal water or residual moisture stemming from raw materials.

Organopolysiloxane Graft Polymer

It is preferred that the composition of the present invention comprises one or more organopolysiloxane graft polymer(s) that has amino and/or quaternary ammonium groups within the graft chain segments in the viewpoint of brightening, shine, and pigment deposition.

Suitable organopolysiloxane graft polymers are known under their CTFA name Polysilicone-1, Polysilicone-9, Polysilicone-14, Polysilicone-16, Polysilicone-18, Polysilicone-19, Polysilicone-24, Polysilicone-25, Polysilicone-26, Polysilicone-27, and Polysilicone-28.

Particularly preferred organopolysiloxane graft polymers in the composition of the present invention are Polysilicone-9 and/or Polysilicone-28 in the viewpoint of brightening, shine, and pigment deposition.

The total concentration of one or more organopolysiloxane graft polymer is preferably 0.01% by weight or more, more preferably 0.05% by weight or more, even more preferably 0.1% by weight or more, calculated to the total of the composition, from the viewpoint of brightening, shine, wear resistance, pigment deposition.

The total concentration of one or more organopolysiloxane graft polymer is preferably 10% by weight or less, more preferably 8% by weight or less, even more preferably 5% by weight or less, calculated to the total of the composition, from the viewpoint of economic efficiency and freedom of formulation design.

In addition, from the viewpoint of attaining the above-mentioned effects, the composition comprises one or more organopolysiloxane graft polymer at a total concentration preferably in the range of 0.01% to 10% by weight, more preferably in the range of 0.05% to 8% by weight, and further more preferably in the range of 0.1% to 5% by weight, calculated to the total of the composition.

Among these ranges, the range of 0.1% to 5% by weight for the concentration of organopolysiloxane graft polymers in the composition is preferable in the viewpoint of easy removability upon 1 shampooing, whereas in the range of 5% to 10% by weight and 8% to 10% by weight, the viewpoint of wear resistance is emphasized.

Pigments

The composition comprises one or more pigment(s) selected from inorganic pigments and/or organic pigments.

In principle, all colored particles are suitable to be used as pigment regardless of their size, shape, and structure with the limitation that these particles are at least partially non-soluble in the organic solvent employed in the composition of the present invention. Preferably the pigments are completely insoluble in said solvent, in viewpoint of-wear resistance.

However, certain average particle sizes are preferred for the purpose of the present invention, in particular to confer a homogenous color to keratin fibers (i.e. pigment deposition), to allow for homogenous film-forming, and to allow for a good removability upon 1 shampooing. A suitable lower average size limit for pigments is 1 μm in diameter measured in powder form with static light scattering equipment (laser diffraction) using the volume-based particle size equation method from the viewpoint of homogenous film-forming and good removability upon 1 shampooing. A suitable instrument for this measurement is the Malver Mastersizer static light scattering instrument equipped with a powder measurement cell. The skilled person notes that for non-spherical particles an equivalent diameter is retrieved by this measurement method and that the preferred size ranges for this invention apply to the equivalent diameters for non-spherical pigments. The upper average limit for pigment particle sizes is suitably 500 μm in diameter measured as above for the lower particle sizes from the viewpoint of brightening and shine.

Thus, the preferred average pigment particle size range is from 1 μm to 500 μm, more preferably it is in the range of 5 μm to 250 μm, further more preferably it is in the range of 10 μm to 100 μm from the viewpoint of homogenous color, homogenous film-forming, and good removability upon 1 shampooing, measured in powder form with static light scattering equipment using the volume-based particle size equation method.

Organic pigments within the meaning of the present invention are salts of organic dyes being at least partially insoluble in the organic solvent with a boiling point in the range of more than 50° C. to 120° C. under atmospheric conditions and 25° C. Suitable organic pigments are selected by the skilled person according to these criteria.

Suitable organic pigments selected from salts of organic dyes being at least partially insoluble in the organic solvent with a boiling point in the range of more than 50° C. to 120° C. under atmospheric conditions and 25° C. are, for example, salts of carmine, aniline black, azo yellow, quinacridone, phthalocyanin blue, sorghum red, CI42090, CI69800, CI69825, CI73000, CI74100, CI74160, CI11680, CI11710, CI15985, CI19140, CI20040, CI21100, CI21108, CI47000, CI47005, CI61565, CI61570, CI74260, CI11725, CI15510, CI45370, CI71105, CI12085, CI12120, CI12370, CI12420, CI12490, CI14700, CI15525, CI15580, CI15620, CI15630, CI15800, CI15850, CI15865, CI15880, CI17200, CI26100, CI45380, CI45410, CI58000, CI73360, CI73915, CI75470, and/or their mixtures, and/or organic dye-adsorbed lakes such as organic lakes of barium, strontium, calcium or aluminium, lakes based on cochineal carmine. Such lakes are known as Blue 1 lake, Yellow 7 lake, Green 3 lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 34 Lake, Red 40 Lake, Yellow 5 Lake, Yellow 6 Lake, Yellow 7 Lake, Yellow 10 Lake, and/or their mixtures.

Inorganic pigments for the composition of the present invention are selected from single constituent material pigments and/or composite material pigments. The term 'single constituent' denotes pigments which are prepared on the basis of one homogenous material that confers the pigment certain chemical and physical properties. The skilled person understands that this definition does not exclude mixed chemical element pigments which constitute one homogenous material.

Suitable single constituent material inorganic pigments are mica, black iron oxide, carbon black, black titanium oxide, red iron oxide, yellow iron hydroxide, titanium iron oxide, titanium dioxide, manganese violet, ultramarine blue, chromium oxides, hydrated chromium oxides, ferric blue, zirconium oxide, bismuth oxychloride, bismuth citrate, zinc oxide, cerium oxide, silicon dioxide, aluminium, aluminium oxide hydrate, aluminium silicate, barium sulfate, calcium carbonate, calcium sulfate, cobalt aluminium oxide, copper powder, gold powder, Prussion blue, magnesium carbonate, manganese (II) phosphate, bronze powder, silver powder, ferric ammonium ferrocyanide, ferric ferrocyanide, henna, zinc sulphide, and/or their mixtures.

The preferred single constituent material pigments are selected from bismuth oxychloride, mica, titanium dioxide, and/or metallic-oxides, and/or their mixtures, as illustrated in examples 1 to 3 from the viewpoint of achieving high brightening, shine, and removability upon 1 shampooing.

The term 'composite material' denotes pigments which consist of more than one constituent material and whose properties are different from those of the single constituents. Typical composite material pigments have a core-shell structure wherein on a single constituent material core one or more different constituent materials are deposited and/or coated on.

Preferably the composite material pigments are selected from bismuth oxychloride and/or metallic-oxides deposited on mica cores and/or titanium dioxide cores, and/or their mixtures from the viewpoint of variability of color conferred to hair as well as brightening and shine.

Suitable composite material pigments are known under their CTFA name mica and bismuth oxychloride and iron oxides, mica and iron oxides, mica and titanium dioxide and iron oxides, mica and iron oxides and titanium oxide and chromium oxide, and/or their mixtures.

More preferably the inorganic pigment is bismuth oxychloride and/or bismuth oxychloride deposited on mica cores, preferably it is known under the CTFA adopted name mica and bismuth oxychloride and iron oxides, in viewpoint of high brightening effect.

It is to be noted that the composition of the present invention may comprise organic dye-adsorbed composite material pigments. Such pigments are known under their CTFA names mica and bismuth oxychloride and carmine, mica and titanium dioxide and carmine, mica and titanium dioxide and carmine and ferric ferrocyanide The composition of the present invention comprises pigments at a total concentration of preferably 0.1% to 10% by weight, more preferably 0.5% to 8% by weight, more preferably 1% to 5% by weight, calculated to the total of the composition, from the viewpoint of sufficiently coloring the hair and removability upon 1 shampooing.

The composition preferably is free of magnesium carbonate.

Propellants

The composition of the present invention is an aerosol composition and comprises one or more propellant(s). In principle, all known cosmetically acceptable propellants are suitable for the present invention. Suitably the propellant is selected from carbon dioxide, dimethylether, n-butane, iso-butane, liquefied petroleum gas, hydrofluorcarbon gases, and/or their mixtures from the viewpoint of small droplet size during spraying, film homogeneity, and removability of color upon 1 shampooing.

The composition comprises propellants at a total concentration of at least 50% by weight, preferably 55% to 90% by weight, more preferably 60% to 85% by weight, calculated to the total of the composition from the viewpoint of smaller droplet size during spraying, better film homogeneity, and enhanced removability of color upon 1 shampooing.

As illustrated in example 2 described below, the inventive composition with a total propellant concentration of at least 50% by weight showed smaller droplet size during spraying, better film homogeneity, and enhanced removability of color upon 1 shampooing in comparison to a composition having less than 50% by weight of propellant.

Depending on the type of aerosol can and type of propellant used, the pressure inside the aerosol can is usually kept below 12 bar, preferably it is around 8.5 bar, further preferably it is below 5 bar from the viewpoint of safety.

To achieve a low pressure within the aerosol can while still yielding a small droplet size during spraying, an organic solvent with a boiling point in the range of 25° C. to 50° C. under atmospheric conditions may be added to the composition of the present invention.

In this case the composition of the present invention comprises one or more propellant(s) and one or more organic solvent(s) with a boiling point in the range of 25° C. to 50° C. under atmospheric conditions, and the total concentration of propellants and organic solvents with a boiling point in the range of 25° C. to 50° C. is in the range of more than 50% to 95% by weight, preferably 55% to 90% by weight, more preferably 60% to 85% by weight, calculated to the total of the composition from the viewpoint of film homogeneity.

Suitable organic solvents having a boiling point in the range of 25° C. to 50° C. under atmospheric conditions are n-pentane and iso-pentane, and/or their mixtures. The preferred one is n-pentane, as illustrated in examples 4-8 from the viewpoint of film homogeneity.

A suitable weight ratio of organic solvent having a boiling point in the range of 25° C. to 50° C. under atmospheric conditions to propellants is in the range of 1 to 5 from the viewpoint of film homogeneity.

Organic Solvents

The composition further comprises one or more cosmetically acceptable organic solvent(s) with a boiling point in the range of more than 50° C. to 120° C. under atmospheric conditions. In principle, all organic solvents fulfilling this requirement are suitable for the composition of the present invention. Preferably one or more organic solvent(s) is/are selected from ethanol, n-propanol, iso-propanol, n-butanol, iso-butanol, and/or their mixtures from the viewpoint of film homogeneity, droplet size during spraying, and removability of color upon 1 shampooing.

Preferably the composition of the present invention comprises one or more cosmetically acceptable organic solvent(s) with a boiling point in the range of 60° C. to 100° C. under atmospheric conditions from the viewpoint of film homogeneity, droplet size during spraying, and removability of color upon 1 shampooing.

The total concentration of organic solvent(s) with a boiling point in the range of more than 50° C. to 120° C., preferably 60° C. to 100° C., under atmospheric conditions preferably is in the range of 5% to 45% by weight, preferably in the range of 10% to 30% by weight, more preferably in the range of 15% to 25% by weight, calculated to the total of the composition from the viewpoint of film homogeneity, droplet size during spraying, and removability of color upon 1 shampooing.

In one aspect of the present invention, the total concentration of organic solvent(s) with a boiling point in the range of more than 50° C. to 120° C., preferably 60° C. to 100° C., under atmospheric conditions is in the range of 5% to 40% by weight and the total concentration of propellant(s) is in the range of 55% to 90% by weight, each calculated to the total of the composition from the viewpoint of film homogeneity, droplet size during spraying, and removability of color upon 1 shampooing.

In another aspect of the present invention, the total concentration of organic solvent(s) with a boiling point in the range of more than 50° C. to 120° C., preferably 60° C. to 100° C., under atmospheric conditions is in the range of 10% to 30% by weight and the total concentration of propellant(s) is in the range of 55% to 85% by weight, each calculated to the total of the composition from the viewpoint of film homogeneity, droplet size during spraying, and removability of color upon 1 shampooing.

In another aspect of the present invention, the total concentration of organic solvent(s) with a boiling point in the range of more than 50° C. to 120° C., preferably 60° C. to 100° C., under atmospheric conditions is in the range of 5% to 30% by weight and the total concentration of propellant(s) is in the range of 60% to 90% by weight, each calculated to the total of the composition from the viewpoint of film homogeneity, droplet size during spraying, and removability of color upon 1 shampooing.

In another aspect of the present invention, the total concentration of organic solvent(s) with a boiling point in the range of more than 50° C. to 120° C., preferably 60° C. to 100° C., under atmospheric conditions is in the range of 5% to 25% by weight and the total concentration of propellant(s) is in the range of 50% to 60% by weight, each calculated to the total of the composition from the viewpoint of film homogeneity, droplet size during spraying, and removability of color upon 1 shampooing.

In another aspect of the present invention, the total concentration of organic solvent(s) with a boiling point in the range of more than 50° C. to 120° C., preferably 60° C. to 100° C., under atmospheric conditions is in the range of 10% to 45% by weight and the total concentration of propellant(s) is in the range of 50% to 85% by weight, each calculated to the total of the composition from the viewpoint of film homogeneity, droplet size during spraying, and removability of color upon 1 shampooing.

In another aspect of the present invention, the total concentration of organic solvent(s) with a boiling point in the range of more than 50° C. to 120° C., preferably 60° C. to 100° C., under atmospheric conditions is in the range of 5% to 10% by weight and the total concentration of propellant(s) is in the range of 55% to 85% by weight, each calculated to the total of the composition from the viewpoint of film homogeneity, droplet size during spraying, and removability of color upon 1 shampooing.

In one aspect of the present invention, the total concentration of organic solvent(s) with a boiling point in the range of more than 50° C. to 120° C., preferably 60° C. to 100° C., under atmospheric conditions is in the range of 5% to 45% by weight and the total concentration of propellant(s) and organic solvents with a boiling point in the range of 25° C. to 50° C. under atmospheric conditions is in the range of 50% to 90% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 10% to 30% by weight and the total concentration of propellant(s) and organic solvents with a boiling point in the range of 25° C. to 50° C. under atmospheric conditions is in the range of 65% to 85% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 10% to 25% by weight and the total concentration of propellant(s) and organic solvents with a boiling point in the range of 25° C. to 50° C. under atmospheric conditions is in the range of 75% to 90% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 10% to 30% by weight and the total concentration of propellant(s) and organic solvents with a boiling point in the range of 25° C. to 50° C. under atmospheric conditions is in the range of 55% to 85% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 5% to 30% by weight and the total concentration of propellant(s) and organic solvents with a boiling point in the range of 25° C. to 50° C. under atmospheric conditions is in the range of 60% to 95% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 5% to 25% by weight and the total concentration of propellant(s) and organic solvents with a boiling point in the range of 25° C. to 50° C. under atmospheric conditions is in the range of 50% to 60% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 10% to 45% by weight and the total concentration of propellant(s) and organic solvents with a boiling point in the range of 25° C. to 50° C. under atmospheric conditions is in the range of 50% to 85% by weight, each calculated to the total of the composition from the viewpoint of film homogeneity, droplet size during spraying, removability of color upon 1 shampooing, and lower pressure in the aerosol can.

In another aspect of the present invention, the total concentration of organic solvent(s) with a boiling point in the range of more than 50° C. to 120° C., preferably 60° C. to 100° C., under atmospheric conditions is in the range of 5% to 10% by weight and the total concentration of propellant(s) and organic solvents with a boiling point in the range of 25° C. to 50° C. under atmospheric conditions is in the range of 55% to 85% by weight, each calculated to the total of the composition from the viewpoint of film homogeneity, droplet size during spraying, removability of color upon 1 shampooing, and lower pressure in the aerosol can.

Lipophilic Compounds

The composition of the present invention preferably comprises one or more lipophilic organic compound(s) which is/are immiscible (for liquid compounds at room temperature and atmospheric conditions) and/or insoluble (for solid/pasty compounds at room temperature and atmospheric conditions) with water at 25° C. and atmospheric conditions and which is/are different from the organopolysiloxane graft polymer in the viewpoint of film homogeneity and pigment deposition.

In principle, all compounds fulfilling the requirements of above are suitable for the present invention.

Preferably, lipophilic compounds are selected from fatty alcohols, fatty acids, waxes, vegetable oils, petrolatum based products, silicones, aminated silicones, and compounds according to the general structure:

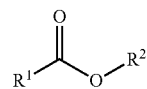

wherein R1 is selected from linear or branched, saturated or unsaturated alkyl with C11 to C21 and optionally modified with 1 hydroxyl group, and R2 is selected from linear or branched, saturated or unsaturated alkyl with C3 to C18, preferably the compound is ethylhexyl hydroxystearate, in the viewpoint of film homogeneity and pigment deposition Suitable fatty alcohols are linear or branched, saturated or unsaturated fatty alcohols with C12 to C22 are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures.

Suitable fatty acids are saturated or unsaturated fatty acids with or without a hydroxyl group. Suitable are myristoleic acid, palmitoleic acid, oleic acidlinoleic acid, arachidonic acid, and/or their mixtures.

Suitable compounds according to the general structure from above:
are isopropyl palmitate, isopropyl myristate, octyl palmitate, isocetyl palmitate, octyl stearate, oleyl oleate, ethylhexyl hydroxystearate, myristyl myristate, behenyl behenate, and/or their mixtures.

Suitable vegetable oils are jojoba oil, avocado oil, sunflower seed oil, walnut oil, peanut oil, olive oil, rapeseed oil, cottonseed oil, palm oil, sesame oil, soybean oil, coconut oil, safflower oil, almond oil, macadamia nut oil, grapefruit seed oil, lemon kernel oil, orange kernel oil, apricot kernel oil, castor oil, and/or their mixtures.

Suitable petrolatum-based products are liquid paraffins, especially paraffinum perliquidum and paraffinum subliquidum, and mineral oil, in particular white mineral oil, and/or their mixtures.

Suitable silicones are dimethylpolysiloxanes, and modified silicones (for example, amino-modified silicones, fluorine-modified silicones, alcohol-modified silicones, polyether-modified silicones, epoxy-modified silicones, or alkyl-modified silicones), but dimethylpolysiloxane, polyether-modified silicones and amino-modified silicones are preferred. Amino-modified silicones are commonly known under their CTFA name amodimethicone.

The dimethylpolysiloxane may be any cyclic or non-cyclic dimethylsiloxane polymer, and examples thereof include SH200 series, BY22-019, BY22-020. BY11-026, B22-029, BY22-034, BY22-050A, BY22-055, BY22-060, BY22-083, FZ-4188 (all by Dow Corning Toray Co., Ltd.) KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

Specific examples of suitable commercially available amodimethicone oils such as SF8452C, SS-3551 (all by Dow Corning Toray Co., Ltd.), KF-8004, KF-8675, and KF-8015 (all by Shin-Etsu Chemical Co. Ltd.), and amodimethicone emulsions such as SM8704C, SM8904, BY22-079, FZ-4671, and FZ-4672 (all by Dow corning Toray Co., Ltd.).

The amino-modified silicone may be any silicone having an amino group or a quaternary ammonium group, and examples thereof include amine-modified silicone oil having all or a part of the terminal hydroxyl groups capped with a methyl group for example, and an amodimethicone which does not have the terminals capped.

The composition may comprise one or more waxes. Suitable non-limiting and preferred examples are petrolatum, ozokerit, carnauba wax, paraffin, lanolin wax, candelila wax, bees wax, microcrystalline wax and cocoglycerides.

The most preferred lipophilic is ethylhexyl hydroxystearate and/or its mixtures with other suitable compounds listed above. In the case of mixtures, the weight ratio of ethylhexyl hydroxystearate to other lipophilic compounds is kept in the range of 0.2 to 5.

The total concentration of lipophilic compounds immiscible and/or insoluble with water at 25° C. and atmospheric conditions and which are different from the organopolysiloxane graft polymer is preferably 0.1% by weight or more, more preferably 0.5% by weight or more, even more preferably 1% by weight or more, calculated to the total of the composition, from the viewpoint of film homogeneity, removability of color upon 1 shampooing.

The total concentration of lipophilic compounds immiscible and/or insoluble with water at 25° C. and atmospheric conditions and which are different from the organopolysiloxane graft polymer is preferably 20% by weight or less, more preferably 15% by weight or less, even more preferably 10% by weight or less, calculated to the total of the composition, from the viewpoint of freedom of formulation design and economic efficiency.

In addition, from the viewpoint of attaining the above-mentioned effects, the total concentration of lipophilic compounds immiscible and/or insoluble with water at 25° C. and atmospheric conditions and which are different from the organopolysiloxane graft polymer is preferably in the range of 0.1% to 20% by weight, more preferably 0.5% to 15% by weight, even more preferably 1% to 10% by weight, calculated to the total of the composition.

Hair Setting Polymers

The composition of the present invention may further comprise one or more hair setting polymer(s) selected from non-ionic and/or cationic and/or anionic and/or amphoteric hair setting polymers in the viewpoint of cosmetic feel and shine.

Suitable non-ionic polymers are vinylpyrrolidon polymers of either homopolymers or copolymers with, particularly, vinylacetate. Those are known with the trade name "Luviskol" as homopolymers Luviskol K 30, K 60 or K 90 as well copolymers Luviskol VA 55, VA 64, Plus from BASF AG and advantage LS-E from ISP.

As amphoteric polymers which can be used alone or in mixture with at least one additional nonionic polymer, reference is here made in particular to copolymers of N-octyl acrylamide, (meth)acrylic acid and tert-butylaminoethyl methacrylate of the type "Amphomer®"; copolymers from methacryloyl ethyl betaine and alkyl methacrylates of the type "Yukaformer®", e.g. butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl (meth)acrylates or mono- or dialkyl aminoalkyl (meth)-acrylamides containing basic groups, in particular amino groups; copolymers from N-octyl acrylamide, methyl methacrylate, hydroxypropyl methacrylate, N-tert-butyl aminoethyl methacrylate and acrylic acid, as well as the copolymers known from U.S. Pat. No. 3,927,199.

Suitable anionic polymers alone or in combination with non-ionic polymers are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinylneodecanoate/crotonic acid copolymers of the type "Resyn®"; sodium acrylate/vinyl alcohol copolymers of the type "Hydagen® F", sodium polystyrene sulfonate, e.g. "Flexan® 130"; ethylacrylate/acrylic acid/N-tert-butyl acrylamide copolymers of the type "Ultrahold®"; vinyl pyrrolidone/vinylacetate/itaconic acid copolymers, acrylic acid/acrylamide copolymers or the sodium salts thereof of the type "Reten®".

Further suitable anionic polymers are acrylate copolymers available under trade name Salcare SC 81, PEG/PPG 25/25 dimethicone/acrylate copolymer available under trade name Luviglex Silk from BASF, Acrylates/t-butylacrylamide copolymer available under trade name Ultrahold Strong, Advantage LC-E which is vinylcaprolactam/PVP/dimethylaminoethylmethacrylate copolymer and VA/crotonates copolymer available under trade name Luviset CA 66.

Suitable cationic polymers are such as Polyquaternium 11, Polyquaternium 16, Polyquaternium 22 and Polyquaternium 28, Polyquaternium 30, Polyquaternium 37, Polyquaternium 36, Polyquaternium 46, Polyquaternium 24, Polyquaternium 67, and Polyquaternium 72.

The total concentration of hair setting polymers in the composition of the present invention is preferably in the range of 0.1 to 15%, more preferably 0.2 to 10%, even more preferably 0.25 to 7.5% and most preferably 0.5 to 7.5% by weight, calculated to the total of the composition from the viewpoint of wear resistance and removability of color upon 1 shampooing.

Hair Direct Dyes

The composition of the present invention may additionally comprise one or more hair direct dye(s) different from pigments well-known in the art, selected from cationic and/or anionic and/or non-ionic hair direct dyes, and/or their mixtures.

Non-limiting examples to cationic dyes are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, HC Blue 18, HC Red 18, and HC Yellow 16.

The preferred anionic hair direct dyes are HC Blue 18, HC Red 18, and HC Yellow 16 in the viewpoint of brightening and shine.

Further suitable dyes for colouring hair within the meaning of the present invention are those of neutral nitro dyes. Suitable non-limiting examples are HC Blue 2, HC Blue 4, HC Blue 5, HC Blue 6, HC Blue 7, HC Blue 8, HC Blue 9, HC Blue 10, HC Blue 11, HC Blue 12, HC Blue 13, HC Brown 1, HC Brown 2, HC Green 1, HC Orange 1, HC Orange 2, HC Orange 3, HC Orange 5, HC Red BN, HC Red 1, HC Red 3, HC Red 7, HC Red 8, HC Red 9, HC Red 10, HC Red 11, HC Red 13, HC Red 54, HC Red 14, HC Violet BS, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. When using direct dyes of various categories, their compatibility must be checked.

Concentration of direct dyes in the compositions of the present invention is within the range of 0.001 to 5%, preferably 0.01 to 3% and more preferably 0.05 to 2%, and most preferably 0.1 to 1% by weight calculated to total composition, calculated to the total of the composition from the viewpoint of brightening and removability of color upon 1 shampooing.

UV Filters

The composition of the present invention may further comprise one or more UV filter(s) which is soluble in the organic solvent selected for the present composition. UV filters or mixtures thereof protect the keratin fibers from damaging effects of sun light. The UV-filters are preferably selected from the following compounds: 4-Aminobenzoic acid and/or esters and/or salts thereof, 2-phenyl benzimidazole-5-sulfonic acid and/or alkali and/or amine salts thereof, 4-dimethyl aminobenzoic acid and/or esters and/or salts thereof, cinnamic acid and/or esters and/or salts thereof, 4-methoxycinnamic acid and/or esters and/or salts thereof, salicylic acid and/or esters and/or salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and/or salts thereof and/or 3-(4'-methyl benzylidene)-DL-campher.

The preferred amount of the UV filter in the composition of the present invention is in the range from 0.01% to 2.5%, more preferably in the range from 0.05% to 1% by weight, calculated to the total of the composition.

The following examples are to illustrate the invention, but not to limit it.

EXAMPLES

Example 1

| Ingredient | Inventive composition [% by weight] | Comparative composition [% by weight] |
|---|---|---|
| Polysilicone-9 | 1.0 | — |
| Trimethylsiloxysilicate | — | 1.0 |
| Bismuth oxychloride | 2.1 | 2.1 |
| Ethylhexyl hydroxystearate | 0.9 | 0.9 |
| Bismuth oxychloride and mica and iron oxides | 1.5 | 1.5 |
| Fragrance | 0.1 | 0.1 |
| n-pentane | 20.0 | 20.0 |
| iso-butane | 50.0 | 50.0 |
| Ethanol | Ad 100.0 | |

The particle sizes of the pigments were in the range of 2 µm to 25 µm as determined by laser diffraction and the average was at 15 µm.

The compositions were prepared without propellants and filled into an aerosol can. Then the aerosol cans were crimped and the cans were charged with propellants.

Human hair streaks (Caucasian, 2 g per bundle, dark color) were purchased from Fischbach+Miller Haar, Laupheim, Germany. The hair streaks were sprayed with the compositions from above for 10 s each. Then the hair streaks were allowed to air dry.

Hair streaks were visually inspected on appearance and each hair streak was pulled 10 times through thumb and pointing finger. The fingers were inspected on color stains. Furthermore, individual hair fibers were analyzed under the microscope at 10× magnification. The hair fibers were photographed and analyzed with Imagej software.

For image analysis, the micrographs were contrast enhanced and the region of interest was set to the shape of the hair fibers in the micrograph. Then the color threshold was set to highlight the spots on the hair fiber which appear with bright metallic shine. A ratio was calculated between the area of the aforementioned metallic spots to the total hair fiber area.

As a result, the hair fibers macroscopically appeared in white-metallic color upon application of the aerosol compositions wherein the hair streak treated with the inventive composition appeared more shiny and brighter in color. The color of the inventive composition was resistant against touch whereas the comparative composition yielded a streak which left color stains on fingers. Microscopic analysis coupled with micrograph analysis revealed that the hair streak treated with the inventive composition had 26.33% of its total area coated with metallic spots whereas the hair streak treated with the comparative composition had coverage of 14.96% of its total area with metallic spots.

Thus, the inventive composition yielded a higher degree of pigment deposition in comparison to the comparative composition. This resulted in a higher degree of shine and brighter color detectable by the naked human eye.

Example 2

| Ingredient | Inventive composition A [% by weight] | Inventive composition B [% by weight] | Comparative composition [% by weight] |
|---|---|---|---|
| Polysilicone-9 | 1.0 | 3.6 | 0.6 |
| Bismuth oxychloride | 2.1 | 7.6 | 1.2 |
| Ethylhexyl hydroxystearate | 0.9 | 3.3 | 0.5 |
| Bismuth oxychloride and mica and iron oxides | 1.5 | 5.5 | 0.9 |
| Fragrance | 0.1 | 0.36 | 0.06 |
| Ethanol | Ad 100.0 | | |
| Stock solution from above | 40 | 11 | 70 |
| n-pentane | — | 29 | — |
| Dimethylether (DME) | 60.0 | 60 | 30.0 |

The particle sizes of the pigments were in the range of 2 µm to 25 µm as determined by laser diffraction and the average was at 15 µm.

The compositions from above were prepared without propellant and n-pentane and filled into an aerosol can. Concentrations were adjusted to ensure an equal total concentration of ingredients in each aerosol composition. Then the aerosol cans were crimped and propellants and n-pentane for inventive composition B were added.

Hair streaks with the same source of example 1 were sprayed with the compositions from above for 10 s each. Then the hair streaks were allowed to air dry.

Film homogeneity onto keratin fibers and droplet size of the aerosol during spraying were visually evaluated by the naked human eye by 10 trained independent experts. Furthermore, after visual inspection of the treated hair streaks, the streaks were shampooed with a commercially available shampoo under the brand name Goldwell Dualsenses Deep Cleansing Shampoo. The shampoo was massaged onto the hair streaks for 60 s and then the hair streaks were rinsed off with lukewarm water and blow dried. The color staining upon shampooing was evaluated by the naked human eye and judged against an untreated hair streak by 10 trained independent experts as well. The experts were provided the following scale for judgement ⊕⊕ excellent
⊕ good
○ poor
○○ unacceptable cosmetic properties The judgements were recorded and the highest number of judgements per treatment group and parameter is presented below:

| Parameter | Inventive composition A | Inventive composition B | Comparative composition |
|---|---|---|---|
| Droplet size during spraying | small | small | large |
| Film homogeneity | ⊕ | ⊕⊕ | ○ |
| Removability of color upon 1 shampooing | ⊕⊕ | ⊕⊕ | ○ |

As a result, experts found the inventive compositions to have smaller droplet sizes during spraying in comparison to the comparative composition. Furthermore, film homogeneity was best for inventive composition B, and judged to be good for inventive composition A. Removability of color upon 1 shampooing in line with the concept of temporary hair coloring was very good for both inventive compositions, corresponding to an excellent judgement by experts. However, the comparative composition did not form a satisfactory film onto hair and additionally could not be easily removed by 1 time shampooing.

Example 3

Inventive composition A of example 2 was prepared as an aerosol and a non-aerosol composition. The aerosol composition was exactly as in example 2, whereas the non-aerosol composition was filled into a commercially available pump spray. Each of the compositions were sprayed onto hair streaks with a target pigment concentration of 0.20 g pigment per streak. The streaks were then allowed to air-dry.

Film homogeneity onto keratin fibers and droplet size of the aerosol during spraying were visually evaluated by the naked human eye by 10 trained independent experts. Natural hair feel and speed of drying were evaluated as a sensory experience, whereas for speed of drying the hair streaks were observed until dry by one practitioner, and hair feel was evaluated by the experts. Furthermore, after visual inspection of the treated hair streaks, the streaks were shampooed with a commercially available shampoo under the brand name Goldwell Dualsenses Deep Cleansing Shampoo. The shampoo was massaged onto the hair streaks for 60 s and then the hair streaks were rinsed off with lukewarm water and blow dried. The color staining upon shampooing was evaluated by the naked human eye and judged against an untreated hair streak by 10 trained independent experts as well. The experts were provided the following scale for judgement ⊕⊕ excellent
⊕ good
○ poor
○○ unacceptable cosmetic properties The judgements were recorded and the highest number of judgements per treatment group and parameter is presented below:

| Parameter | Inventive composition A | Non-aerosol composition |
|---|---|---|
| Speed of drying | ⊕⊕ | ○○ (very wet) |
| Pigment deposition | ⊕⊕ | ○ (pigment clusters) |
| Droplet size during spraying | small | large |
| Film homogeneity | ⊕⊕ | ○○ |
| Natural hair feel | ⊕ | ○ |
| Removability of color upon 1 shampooing | ⊕⊕ | ⊕ |

As presented above, the non-aerosol composition is inferior in all test criteria and does not lead to the technical effects of the aerosol.

Example 4

| | % by weight |
|---|---|
| Polysilicone-9 | 3.0 |
| Bismuth oxychloride and mica and iron oxides | 1.0 |
| Fragrance | 0.1 |
| n-pentane | 20 |
| Liquefied petroleum gas | 50 |
| Ethanol | ad 100.0 |

The particle sizes of the pigments were in the range of 2 μm to 50 μm as determined by laser diffraction and the average was at 30 μm.

The composition was prepared without the propellants and filled into an aerosol can. Then the aerosol cans were crimped and the propellants were added. The composition was sprayed onto hair streaks and yielded a good color result. Moreover, temporary styling of hair streaks was possible.

Example 5

| | % by weight |
|---|---|
| Polysilicone-9 | 3.0 |
| Bismuth oxychloride | 0.7 |
| Ethylhexyl hydroxystearate | 0.3 |
| Mica | 0.25 |
| Iron oxide | 0.25 |
| PVP K90 | 1.0 |
| Fragrance | 0.1 |
| n-pentane | 20 |
| Liquefied petroleum gas | 50 |
| Iso-propanol | ad 100.0 |

The particle sizes of the pigments were in the range of 2 μm to 25 μm as determined by laser diffraction and the average was at 15 μm.

The composition was prepared without the propellants and filled into an aerosol can. Then the aerosol cans were crimped and the propellants were added. The composition was sprayed onto hair streaks and yielded a good color result. Moreover, temporary styling of hair streaks was possible.

The butyl ester of PVM/MA copolymer was replaced with acrylates copolymer and delivered a stable aerosol composition. The composition was sprayed onto hair streaks and yielded a good color result. Moreover, temporary styling of hair streaks was possible with a comb.

Example 6

| | % by weight |
|---|---|
| Polysilicone-9 | 1.0 |
| Polysilicone-28 | 1.0 |
| Bismuth oxychloride and mica and iron oxides | 1.5 |
| Olive oil | 1.0 |
| Cyclopentasiloxane | 0.5 |
| VA/Crotonates/Vinyl Neodecanoate Copolymer* | 5.0 |
| Fragrance | 0.1 |
| n-pentane | 20 |
| Dimethylether | 60 |
| Ethanol | ad 100.0 |

*Luviset CAN purchased from BASF Corp.

The particle sizes of the pigments were in the range of 1 μm to 100 μm as determined by laser diffraction and the average was at 65 μm.

The composition was prepared without the propellants and filled into an aerosol can. Then the aerosol cans were crimped and the propellants were added. The composition was sprayed onto previously washed and shampooed hair streaks. The composition was sprayed onto hair streaks and yielded a good color result. Moreover, without drying of the composition onto the hair streak, temporary styling of the hair streak was possible with the use of a flat-iron set to a temperature of 180° C. wherein the hair streak was treated with 5 strokes of the flat-iron.

Dimethylether in the composition above was replaced with isobutane or isopropane. Both yielded a stable aerosol composition. The composition was sprayed onto hair streaks. The composition was sprayed onto hair streaks and yielded a good color result. Moreover, temporary styling of hair streaks with a flat-iron was possible as well.

Example 7

|  | % by weight |
| --- | --- |
| Polysilicone-9 | 6.0 |
| Polysilicone-28 | 0.5 |
| Bismuth oxychloride | 1.5 |
| Ethylhexyl hydroxystearate | 0.7 |
| Titanium dioxide | 0.5 |
| Mica | 0.25 |
| Iron oxide | 0.25 |
| VA/Crotonates/Vinyl Neodecanoate Copolymer* | 3.0 |
| Dimethyl Acrylamide/Hydroxyethyl Acrylate/Methoxyethyl Acrylate Copolymer** | 2.0 |
| Amodimethicone | 0.2 |
| Fragrance | 0.1 |
| n-pentane | 20 |
| Hydrofluorcarbon 152a | 55 |
| Ethanol | ad 100.0 |

*Luviset CAN purchased from BASF Corp.
**PLASCIZE L-2700 purchased from DKSH Corp.

The particle sizes of the pigments were in the range of 10 μm to 50 μm as determined by laser diffraction and the average was at 25 μm.

The composition was prepared without the propellants and filled into an aerosol can. Then the aerosol cans were crimped and the propellants were added. The composition was sprayed onto hair streaks and yielded a good color result. Moreover, temporary styling of hair streaks was possible with a brush.

The following examples are within the scope of the present invention:

Example 8

|  | % by weight |
| --- | --- |
| Polysilicone-14 | 0.1 |
| Polysilicone-16 | 0.5 |
| Aluminium silicate | 0.3 |
| Yellow 7 lake | 0.25 |
| Barium sulfate | 0.05 |
| Bees wax | 0.5 |
| White mineral oil | 0.25 |
| Fragrance | 0.1 |

-continued

|  | % by weight |
| --- | --- |
| HC Blue 18 | 0.1 |
| HC Red 18 | 0.1 |
| n-pentane | 20 |
| Dimethylether | 60 |
| Ethanol | ad 100.0 |

Example 9

|  | % by weight |
| --- | --- |
| Polysilicone-9 | 1.5 |
| Polysilicone-28 | 0.75 |
| Bismuth oxychloride and mica and iron oxides | 0.50 |
| Titanium dioxide and iron oxides | 0.1 |
| White mineral oil | 0.75 |
| Fragrance | 0.1 |
| HC Blue 18 | 0.1 |
| HC Yellow 16 | 0.1 |
| Dimethylether | 60 |
| Isoproanol | ad 100.0 |

The invention claimed is:

1. A cosmetic aerosol composition for keratin fibers, comprising:
   one or more organopolysiloxane graft polymer(s) selected from the group consisting of Polysilicone 9 and Polysilicone 28,
   one or more pigment(s),
   one or more cosmetically acceptable organic solvent(s) with a boiling point in the range of more than 50° C. to 120° C. under atmospheric conditions, and
   one or more propellant(s) at a total concentration of at least 50% by weight, calculated to a total weight of the composition,
   wherein the composition comprises less than 5% by weight of water, calculated to the total weight of the composition.

2. The composition according to claim 1, wherein the one or more pigment(s) are inorganic pigments and/or organic pigments.

3. The composition according to claim 1, wherein the one or more organic pigments are salts of organic dyes being at least partially insoluble in the organic solvent under atmospheric conditions and 25° C., and/or organic lakes, and/or their mixtures.

4. The composition according to claim 1, wherein the one or more pigment(s) are inorganic pigments that are single constituent material pigments and/or composite material pigments.

5. The composition according to claim 1, wherein the one or more pigment(s) comprise an inorganic pigment that is bismuth oxychloride and/or bismuth oxychloride deposited on mica cores.

6. The composition according to claim 1, comprising pigments at a total concentration of 0.01% to 10% by weight, calculated to the total weight of the composition.

7. The composition according to claim 1, wherein the one or more propellant(s) is/are selected from the group consisting of carbon dioxide, dimethylether, n-butane, isobutane, liquefied petroleum gas, and hydrofluorcarbon gases, and the total concentration of propellants is in the range of 55% to 90% by weight, calculated to the total weight of the composition.

8. The composition according to claim 1, further comprising one or more organic solvent(s) with a boiling point in the range of 25° C. to 50° C. under atmospheric conditions, wherein a total concentration of propellants and organic solvents with a boiling point in the range of 25° C. to 50° C. is in the range of more than 50% to 95% by weight, calculated to the total weight of the composition.

9. The composition according to claim 1, wherein a total concentration of organic solvent(s) with a boiling point in the range of more than 50° C. to 120° C. under atmospheric conditions is in a range of 5% to 45% by weight, calculated to the total weight of the composition.

10. The composition according to claim 1, further comprising one or more lipophilic organic compound(s) which is/are immiscible and/or insoluble with water at 25° C. and atmospheric conditions and which is/are different from the organopolysiloxane graft polymer.

11. The composition according to claim 10, wherein the one or more lipophilic compound(s) is/are selected from the group consisting of fatty alcohols, fatty acids, waxes, vegetable oils, petrolatum based products, silicones, aminated silicones, and compounds according to structure:

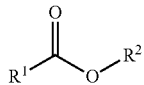

wherein R1 is linear or branched, saturated or unsaturated alkyl with C11 to C21 and optionally modified with 1 hydroxyl group, and R2 is linear or branched, saturated or unsaturated alkyl with C3 to C18.

12. The composition according to claim 1, further comprising one or more hair setting polymer(s) that is/are non-ionic and/or cationic and/or anionic and/or amphoteric hair setting polymers.

13. The composition according to claim 1, further comprising one or more hair direct dye(s) different from pigments, that is/are cationic and/or anionic and/or non-ionic hair direct dyes.

14. A method for dyeing keratin fibers, comprising:
a) optionally washing and drying the keratin fibers,
b) applying the cosmetic aerosol composition of claim 1 to dry keratin fibers, and
d) optionally treating the keratin fibers with a comb, brush, flat-iron and/or round-iron at a temperature in the range of 50° C. to 230° C.

15. The composition according to claim 1, wherein the one or more organic pigments are organic lakes selected from the group consisting of Blue 1 lake, Yellow 7 lake, Green 3 lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 34 Lake, Red 40 Lake, Yellow 5 Lake, Yellow 6 Lake, Yellow 7 Lake, and Yellow 10 Lake.

16. The composition according to claim 1, comprising pigments at a total concentration of 1% to 5% by weight, calculated to the total weight of the composition.

17. The composition according to claim 1, wherein the one or more propellant(s) is/are selected from the group consisting of carbon dioxide, dimethylether, n-butane, isobutane, liquefied petroleum gas, and hydrofluorcarbon gases, and the total concentration of propellants is in the range of 60% to 85% by weight, calculated to the total weight of the composition.

18. The composition according to claim 10, wherein the one or more lipophilic compound(s) comprise ethylhexyl hydroxystearate.

* * * * *